US012653589B2

(12) United States Patent
Oldakowska et al.

(10) Patent No.: US 12,653,589 B2
(45) Date of Patent: Jun. 16, 2026

(54) EXPANDABLE FASTENER FOR ORTHOPAEDIC APPLICATIONS

(71) Applicant: CURTIN UNIVERSITY, Bentley, WA (US)

(72) Inventors: Intan Camellia Watono Oldakowska, Applecross (AU); Matthew Peter Oldakowski, Applecross (AU)

(73) Assignee: Curtin University, Bentley (AU)

( * ) Notice: Subject to any disclaimer, the term of this patent is extended or adjusted under 35 U.S.C. 154(b) by 0 days.

(21) Appl. No.: 18/708,119

(22) PCT Filed: Oct. 24, 2022

(86) PCT No.: PCT/AU2022/051274
§ 371 (c)(1),
(2) Date: May 7, 2024

(87) PCT Pub. No.: WO2023/077182
PCT Pub. Date: May 11, 2023

(65) Prior Publication Data
US 2024/0423685 A1      Dec. 26, 2024

(30) Foreign Application Priority Data

Nov. 8, 2021    (AU) ................................. 2021903563

(51) Int. Cl.
*A61B 17/86*        (2006.01)
*A61B 17/74*        (2006.01)
*A61B 17/84*        (2006.01)
(52) U.S. Cl.
CPC ........ *A61B 17/844* (2013.01); *A61B 17/8685* (2013.01)

(58) Field of Classification Search
CPC .............. A61B 17/844; A61B 17/8685; A61B 17/7233; A61B 17/725; A61B 17/7266; A61B 2017/8655
See application file for complete search history.

(56) References Cited

U.S. PATENT DOCUMENTS 5,057,103 A      10/1991  Davis
9,314,282 B2 *    4/2016  Kecman ............... A61B 17/155
(Continued)

*Primary Examiner* — Tracy L Kamikawa
(74) *Attorney, Agent, or Firm* — FULLER IP LAW LLC; Rodney J. Fuller

(57)        ABSTRACT

The present disclosure relates to an expandable fastener for orthopaedic applications. The fastener is arranged for fastening when positioned in a bore hole in bone and comprises a body having an axis. The fastener further comprises an expansion portion moveable between a contracted configuration and an expanded configuration and arranged such that the expansion portion urges outwardly from the axis of the body towards the bone surrounding the bore hole when moving towards the expanded configuration. In addition, the fastener comprises a coupling member for coupling to the expansion portion. The coupling member is moveable along the axis of the body. The fastener also comprises an actuator movable along the axis of the body and arranged to move the coupling member along the axis of the body. One of the coupling member and the expansion portion comprises a recess and the other one of the coupling member and the expansion portion comprises a projection. The projection and the recess are arranged such that a hinge is formed when the projection is received in the recess and the expansion portion is movable about an axis through the projection. The projection is insertable into the recess in a first angular orientation of an axis of the expansion portion relative to the axis of the body and is prevented from retracting out of the recess in a second angular orientation of the axis of the expansion portion relative to the axis of the body.

17 Claims, 8 Drawing Sheets

(56)         References Cited

U.S. PATENT DOCUMENTS

| | | | |
|---|---|---|---|
| 10,485,591 B2 * | 11/2019 | Lequette | A61B 17/72 |
| 2013/0144345 A1 | 6/2013 | Felder et al. | |
| 2015/0045841 A1 | 2/2015 | Oglaza et al. | |
| 2017/0311997 A1 | 11/2017 | Lequette et al. | |
| 2018/0071102 A1 | 3/2018 | Bianchi et al. | |
| 2019/0083152 A1 | 3/2019 | Kuster et al. | |
| 2021/0038275 A1 * | 2/2021 | Kinane | A61B 17/742 |

* cited by examiner

EXPANDABLE FASTENER FOR ORTHOPAEDIC APPLICATIONS

CROSS-REFERENCE TO RELATED APPLICATIONS

This application is the U.S. National Stage of International Patent Application No. PCT/AU2022/051274, filed on Oct. 24, 2022, which claims the benefit of and priority to Australian Patent Application No. 2021903563, filed on Nov. 8, 2021, the contents of each of which are hereby incorporated by reference in their entireties.

FIELD OF THE INVENTION

The present invention relates to an expandable fastener for orthopaedic applications.

BACKGROUND OF THE INVENTION

Expandable fasteners have been used for orthopaedic applications in order to increase fixation strength and decrease the risk of failures. Such expandable fasteners are inserted into holes in bone in which they expand and secure broken portions of the bone. Expandable fasteners of this type can also be used for applications in which they interface with, or are coupled to, another device such as plates and rods. For example, expandable fasteners are used when securing portions of the femur when the femur neck is fractured and may also be used for securing femur nails in the femur.

After the bone has healed, the expandable fasteners are usually removed from the bore holes in order to avoid leaving a foreign body inside the human body. However, fastener, and especially expandable fasteners, present hollows and asperities, into which bone may grow, preventing the ability to remove the fasteners. Removal of the fasteners requires contracting the fasteners from an expanded configuration to a contracted configuration. However, ingrowth of bone often makes it impossible to contract the fasteners, which results in complications.

The present applicant's U.S. patent Ser. No. 10/729,480 discloses an expandable fastener arranged to reduce ingrowth of bone and facilitate removal of the fastener. U.S. patent Ser. No. 10/729,480 is herewith incorporated by cross-reference.

The present invention provides further improvement.

SUMMARY OF THE INVENTION

In a first aspect of the present invention there is provided an expandable fastener for orthopaedic applications, the fastener being arranged for fastening when positioned in a bore hole in bone and comprising:

a body having an axis;

an expansion portion moveable between a contracted configuration and an expanded configuration and arranged such that the expansion portion urges outwardly from the axis of the body towards the bone surrounding the bore hole when moving towards the expanded configuration;

a coupling member for coupling to the expansion portion, the coupling member being moveable along the axis of the body; and an actuator movable along the axis of the body and arranged to move the coupling member along the axis of the body;

wherein one of the coupling member and the expansion portion comprises a recess and the other one of the coupling member and the expansion portion comprises a projection, wherein the projection and the recess are arranged such that a hinge is formed when the projection is received in the recess and the expansion portion is movable about an axis through the projection, and wherein the projection is insertable into the recess in a first angular orientation of an axis of the expansion portion relative to the axis of the body and is prevented from retracting out of the recess in a second angular orientation of the axis of the expansion portion relative to the axis of the body.

In one specific embodiment the actuator is arranged to abut with the coupling member. The actuator may comprise an outer thread, the body may comprise an inner thread and the actuator may in use threadedly engage with the body. The fastener may further comprise an actuating element positioned such that, when the coupling element and the expansion portion are moved towards the actuating element and the expansion portion contacts the actuating element, further movement of the expansion portion towards the actuating element urges an end of the expansion portion away from the axis of the body to transfer the actuating portion into an expanded configuration.

The actuating element may have an actuating surface and the expansion portion may have an inner expansion surface that glides on the actuating surface when the expansion portion is moved from a configuration of minimal or no expansion towards the expanded configuration. The actuating surface and the expansion surface may have matching shapes at the contact area within which the expansion surface glides over the actuating surface whereby the penetration of bone between the expansion surface and the actuating surface is avoided when the expansion portion is moved towards the expansion configuration in bone, which avoids or at least reduces ingrowth of bone. In one specific variation the fastener is arranged such that the actuating surface and expansion surface are always in contact when the expansion portion transitions from an unexpanded configuration to the expanded configuration to avoid or at least reduce likelihood of penetration of bone between the actuating surface and the expansion surface.

The body may comprise a slot and the expansion portion may project through the slot when the expansion portion is in the expanded configuration. The expansion portion and the slot may be shaped such that the expansion portion contacts the slot or the slot and the expansion portion may form a gap of 20-500 μm thereby preventing or reducing likelihood of ingrowth of bone.

The expansion portion may be a single expansion portion. Alternatively, the expansion portion may be one of a plurality of expansion portions and the slot may be one of a plurality of slots. In one embodiment the fastener comprises 2, 3 or 4 expansion portions. The expansion portions may each comprise a projection and the coupling member may comprise respective recesses for receiving the projections. Alternatively, the expansion portions may each comprise a projection and the coupling member may comprise a single recess for receiving all projections. For example, the coupling member may be substantially ring-shaped and the single recess may be provided in the form of a ring-shaped groove.

The fastener may have a normal configuration in which the expansion portion is in an unexpanded configuration and the axis of the expansion portion is oriented along the axis of the body. The fastener may be arranged such that, when in the normal configuration, movement of the expansion portion to an orientation across the axis of the body is necessary to reach an angular orientation within the first angular range in which the expansion portion can be decoupled from the coupling portion.

The fastener may alternatively be arranged such that, when in the normal configuration, movement of the expansion portion to an over-expanded configuration orientation is necessary to reach an angular orientation within the first angular range in which the expansion portion can be decoupled from the coupling portion.

In one embodiment the expansion portion has the projection and the coupling member has the recess. The recess and/or the projection may be shaped such that surfaces of the projection and the recess frictionally engage with each other when the projection is positioned within the recess and friction between the projection and the recess increases when the expansion portion is moved towards the expanded configuration from the normal configuration in which the expansion portion is in an unexpanded configuration. A person skilled in the art will appreciate that friction between the projection and the recess may be generated in various different ways. For example, friction may be generated by a surface roughness of a contact surfaces of the recess and/or the projection. Alternatively, friction may be caused by shaping the contact surfaces of the projection and the recess such that friction increases when the expansion portion is moved towards the expanded configuration from the normal configuration in which the expansion portion is in an unexpanded configuration.

The fastener may further comprise a blocking portion moveable into a blocking configuration, which may be provided in the form of an end portion of the actuator which is insertable into a portion of the body of the fastener and which may be in a blocking configuration when inserted and may then be positioned adjacent to the expansion portion. The blocking portion may be positioned to block movement of the expansion portion into the first angular range when the expansion portion is in the normal or expanded configuration thereby preventing that the expansion portion can de-couple from the coupling member. Further, the blocking portion may be arranged for blocking the expansion portion from retracting from the expanded configuration into an unexpanded configuration when in the blocking configuration.

The fastener may be arranged for projecting through a portion of an orthopaedic nail or another orthopaedic device and the expansion portion may have an outer recess arranged to reduce likelihood of jamming with a wall portion of the orthopaedic nail or other orthopaedic device when the expansion portion moves from the expanded configuration to towards the normal configuration to enable retraction of the fastener out of the bore hole and through the portion of the orthopaedic nail or other orthopaedic device. Further, the outer recess of expansion portion may be arranged to reduce likelihood of jamming when the expansion portion transitions from the unexpanded configuration to an expanded configuration.

The expansion portion may comprise a lock-stop portion at which the expansion portion abuts with another portion of the fastener when the expansion portion is in an expanded configuration, wherein the lock-stop portion is arranged to avoid over-expansion of the expansion portion and minimize a gap between the expansion portion and another portion of the fastener thereby avoiding or reducing likelihood of ingrowth of bone.

The fastener comprises in one specific embodiment a spring-loaded mechanism which biases the expansion portion away from the expanded configuration towards the normal configuration or another unexpanded configuration. The spring-loaded mechanism may for example comprise a cantilever spring that may be arranged for engagement with a portion of the fastener. The spring-loaded mechanism is in one example arranged for engagement with an outer portion of the coupling member.

The actuator may have an extension that is arranged to frictionally engage with an inner portion of the expansion portion when the expansion portion is in the expanded configuration and, because of the frictional engagement, the expansion portion is moved or dragged from the expanded configuration towards the normal or unexpanded configuration when the actuator is moved along the axis of the body in a direction out of the body and away from the actuating element. The above-described spring-loaded mechanism typically is arranged to facilitate frictional engagement between the inner surface of the expansion portion and the actuator. The actuator and/or an inner surface of the expansion portion may also comprise features such as projections that enable engagement of the actuator and the expansion portion.

The expansion portion and/or the slot may be shaped such that bone is pushed away from the axis of the fastener when the expansion portion is moved from the expanded configuration towards an unexpanded configuration whereby expansion portion and/or the slot are arranged such that bone accumulation at the expansion portion inside the slot, which could stop the expansion portion to fully retract, is substantially avoided.

The expansion portion may also have distal portion or a tip that is shaped such that bone is compacted at the distal end or tip when the expansion portion is moved from the unexpanded configuration to the expanded configuration when the fastener is positioned in a bore hole in bone. The compacted bone may provide reinforcement and may stimulate bone growth to the area surrounding the distal portion or tip of the expansion portion.

In one embodiment the expansion portion has a modified external surface at the distal end or tip of the expansion portion. The modified external surface is in this embodiment arranged to promote growth of bone at the distal end or tip to prevent migration of the fastener (and/or the orthopaedic device which the fastener in use fastens in bone) further into bone than desired when pressure is applied such as by a patient (for example to prevent screw migration upwards into the hip joint when a patient walks after hip joint surgery). For example, the modified external surface of the expansion portion may have a coating which promotes bone growth such as comprising Hydroxyapatite or may have an increased surface porosity (increased surface porosity relative to a surface porosity of another surface of the expansion portion) to promote bone growth at the distal end or tip of the expansion portion.

Further, the outer surface of the expansion portion may be curved in a plane perpendicular to the axis of the expansion portion and shaped to approximate a curvature of the body of the fastener in a plane perpendicular to the axis of the fastener whereby the expansion portion is arranged such that, when in the unexpanded configuration catching of bone by the expansion portion or portions of the slot of the fastener is substantially avoided when the fastener is removed from the bore hole in bone.

The expansion portion may further have a surface that abuts against another surface of the fastener and is shaped such that the expansion portion is moved from the expanded configuration towards the normal configuration when the coupling element with the actuator is moved along the axis of the body and in a direction out of the body of the fastener.

The invention will be more fully understood from the following description of specific embodiments of the invention. The description is provided with reference to the accompanying drawings.

BRIEF DESCRIPTION OF THE DRAWINGS

FIGS. 2(a) to 8 show components of the expandable fastener in accordance with embodiments of the present invention.

DETAILED DESCRIPTION OF EMBODIMENTS

Embodiments of the present invention generally relate to an expandable fastener. The fastener may be used for orthopaedic applications to secure stabilisation members used to stabilise fractured bones or to fuse joints. In one example the fastener is arranged to secure a femur nail or plate to bone for treatment of a femur fracture. A person skilled in the art will, however, appreciate that the fastener in accordance with embodiment of the present invention has various further orthopaedic applications.

Figure 1:
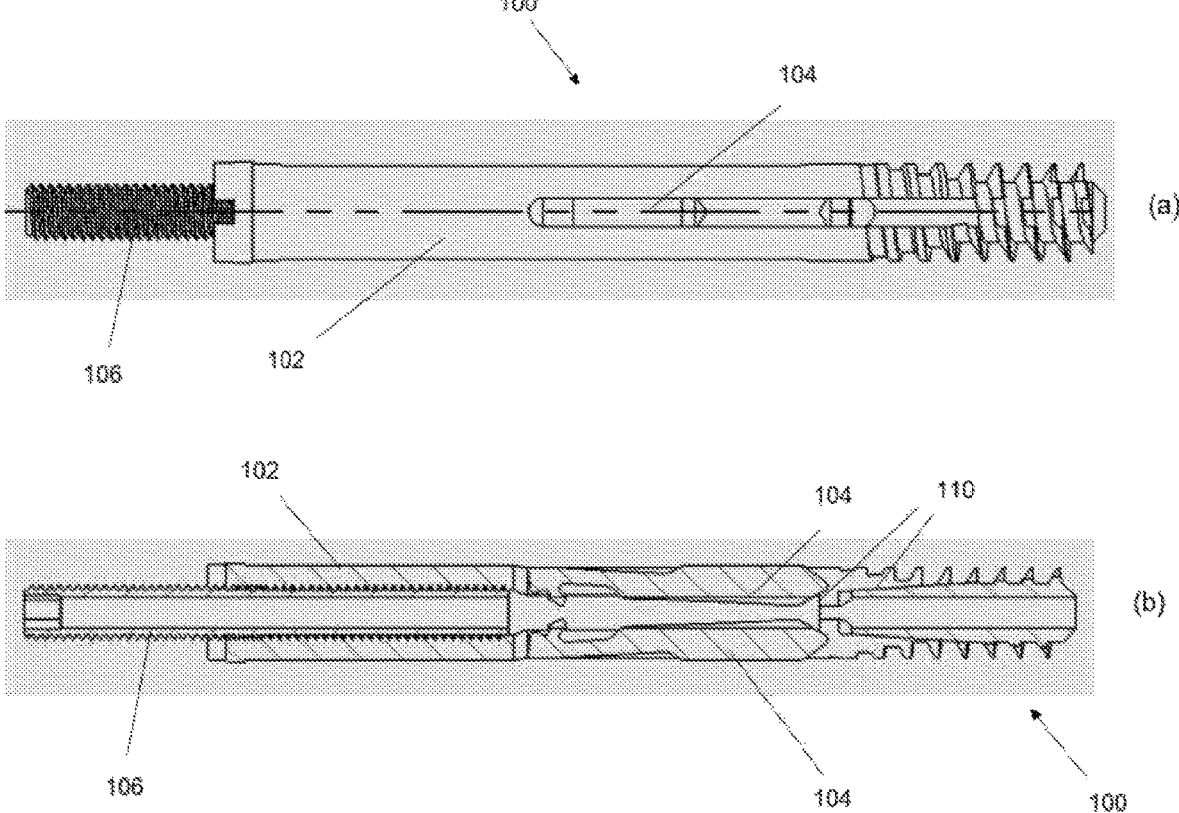
FIG. 1(a) is a side view and FIG. 1(b) is a cross-sectional view of an expandable fastener for orthopaedic applications in accordance with an embodiment of the present invention.

Referring initially to FIGS. 1(a) and 1(b), the orthopaedic fastener is now described. FIGS. 1(a) and 1(b) show the fastener 100 having a body 102 and expansion portions 104 that are moveable between a contracted and an expanded configuration. When the fastener 100 is positioned in a bore hole in bone and the expansion portions 104 are moved towards the expanded configuration, the expansion portions 104 urge outwardly from an axis of the body 102 towards the bone surrounding the bore hole.

The fastener 100 may have a single expansion portion, but typically has 2, 3 or 4 expansion portions and is arranged such that ingrowth of bone between the expansion portions 104 and the body 102 or into the internal section of the body 102 is avoided when the expansion portions 104 are in the expanded configuration.

Figure 2:
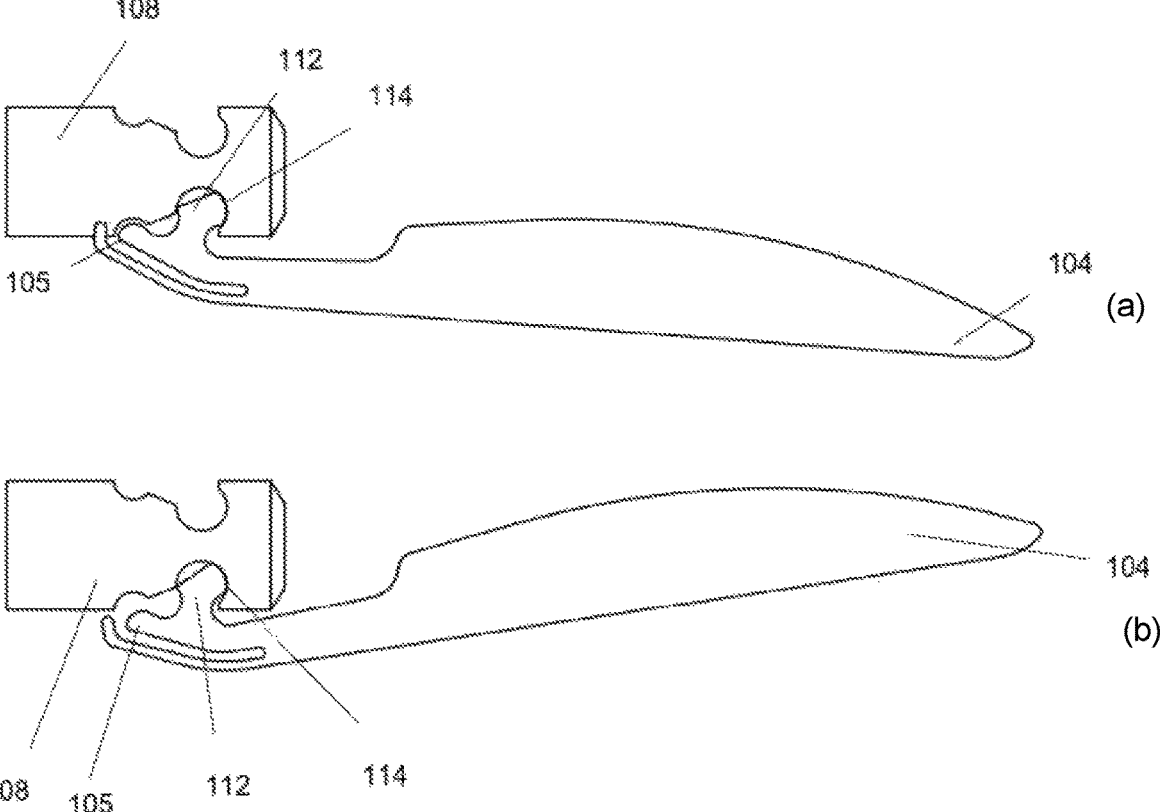

The fastener 100 has an actuator 106 with an outer thread and the body 102 has a matching inner thread. When the outer thread of the actuator 106 engages with the inner thread of the body 102 and the actuator 106 is screwed inwardly, the actuator 106 eventually abuts against a coupling member 108 shown in FIGS. 2(a) and 2(b). The coupling member 108 is slidable along an axis of the body 102 and coupled to the expansion portions 104 by hinges. The fastener 100 also comprises an actuating element 110 (which includes a ramp-shaped portion) and, when the actuator 106 pushes the coupling member 108 with engaged expansion portions 104, the expansion portions 104 engage with the actuating element 110 and are pushed outwardly towards the expanded configuration.

The expansion portions 104 project through slots in the body 102 in a manner such that gaps are substantially avoided or minimised and thereby ingrowth of bone is avoided. This will be described in detail further below.

In the described embodiment the coupling member 108 has a plurality of recesses 114 for receiving respective projections 112 of the expansion portions 104 such that hinges is formed (which may also be referred to as linear bearings). As may be seen from FIGS. 3(a) and 3(b), the projections 112 are shaped such that the projections 112 are insertable into the recesses 114 only in a specific first angular orientation of the expansion portions 104 (and consequently the projections 112) relative to the axis of the body 102 and are prevented from retracting out of the recesses 114 in any other angular orientation of the expansion portion 104 relative to the axis of the body 102. In this embodiment this is achieved by removing a portion 113 of the generally circular projection 112. The portion 113 is removed from the projection 114 along straight cut 115 and at a location selected such that projection 112 can only be retracted (and the expansion portion 104 decoupled from the coupling member 108) when the expansion portion 104 is in an "under-expanded" configuration in which the expansion portion 104 projects in a direction across the axis of the body 102. In a variation of the described embodiment the straight cut 115 has a location selected such that projection 112 can only be retracted (and the expansion portion 104 decoupled from the coupling member 108) when the expansion portion 104 is in an "over-expanded" configuration in which the expansion portion 104 projects in a direction away the axis of the body 102.

Figure 3:
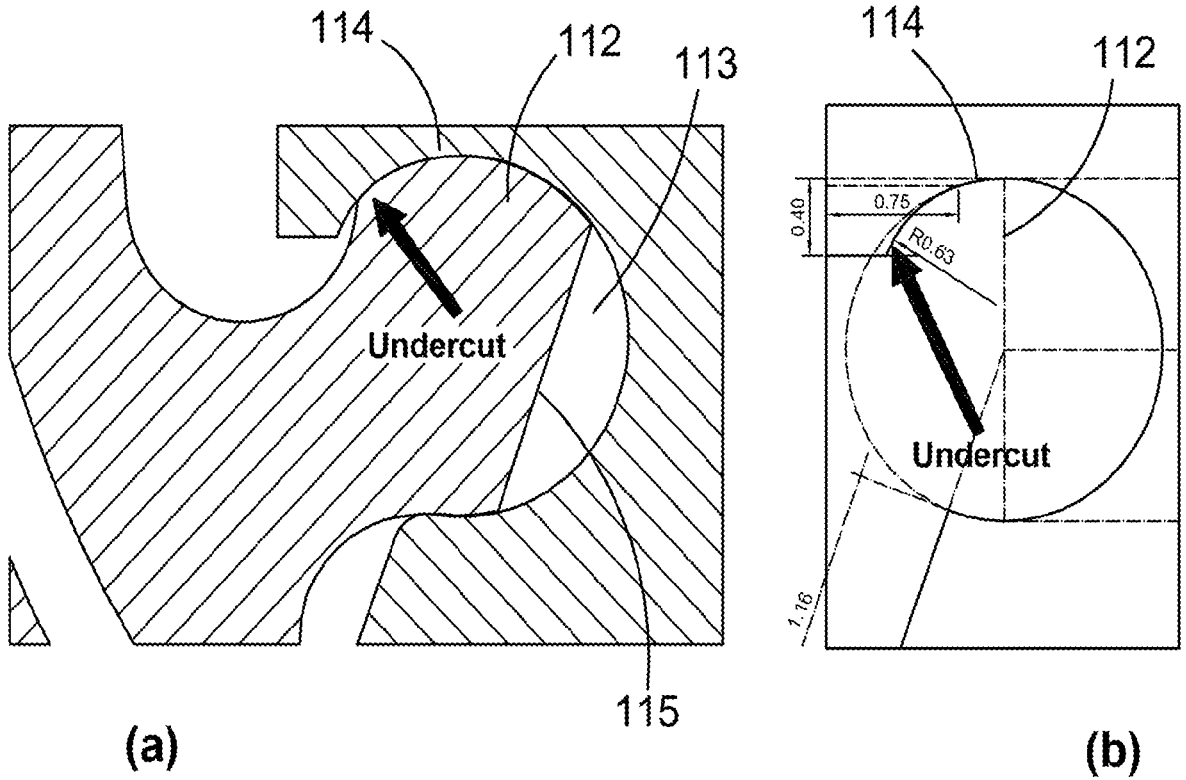

In one embodiment the projections 112 and the recesses 114 are shaped such that surfaces of the projections 112 and the recesses 114 frictionally engage when the projections 112 are positioned within the recesses 114 and friction between the projections 112 and the recess 114 increases when the expansion portions 104 are moved towards the expanded configuration from a normal configuration in which the expansion portions are in an unexpanded configuration. In this embodiment this is achieved by forming the projections 112 and the recesses 114 with a cross-sectional shape that is slightly off a circular shape and comprises an "undercut" region as indicated in FIGS. 3(a) and (b).

Figure 4:
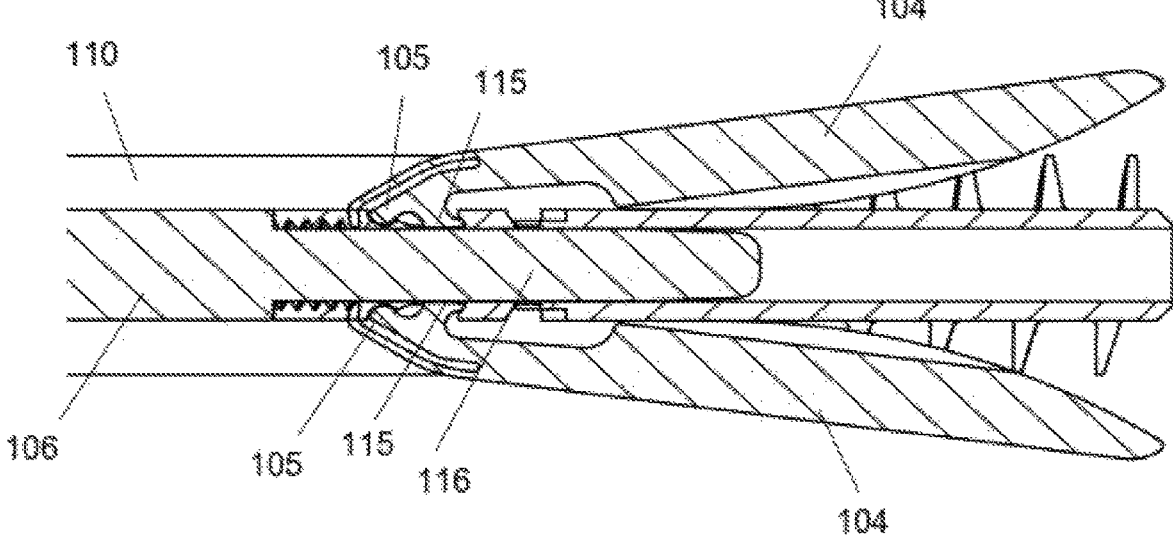

Referring now to FIG. 4, further components of the fastener 100 are described and like components are given like reference numerals. The actuator 106 comprises in this embodiment an extension 116, which limits the possible angular movement of each expansion portion 104 when the extension 116 is inserted into the body 102 and positioned to abut with an inner surface of each expansion portion 104. When the inner surfaces of the extension portions 104 abut against the extension 116, the expansion portions 104 cannot be rotated towards the axis of the body into the first angular range within which the projections 112 can be detracted from the recesses 114 and the expansion portions 104 can be decoupled from the coupling member 108.

The actuator 106 with the extension 116 is shaped to frictionally engage with an inner surface of the expansion portions 104 when the expansion portions 104 are in the expanded configuration, and, because of the frictional engagement, the expansion portions 104 are moved from the expanded configuration towards the normal or unexpanded configuration when the actuator 106 is moved along the axis of the body in a direction out of the body 102, which facilitates removal of the fastener 100 out of a bore hole in bone. Further, the actuator 106 or the inner surface of the expansion portions 104 may also comprise hook-like features or projections (not shown) that enable engagement of the actuator 106 and the expansion portions 104.

The expansion portions 104 also have limit-stop portions 105, which abut against the coupling member 108 when in the expanded configuration and prevent over-expansion. The limit-stop portions 105 have for example a convex shape and the coupling portions may have a mating concave shape, which may be seen for example in FIG. 2. The abutment of the limit-stop portion 105 against the coupling member 108 in the expanded configuration also substantially avoids ingrowth of bone at this location of the fastener.

As described above, the projections 112 have straight cuts 115, which can be seen in FIGS. 3(a) and (b). As illustrated in FIG. 4, the straight cuts 115 are positioned such that, when the expansion portions 104 are in the expanded configuration, the straight cuts 115 abut against the extension 116 of the actuator 106, which avoids that the expansion portions 104 can over-expanded as long as the actuator 106 with the extension 116 is fully inserted into the fastener.

Figure 5:
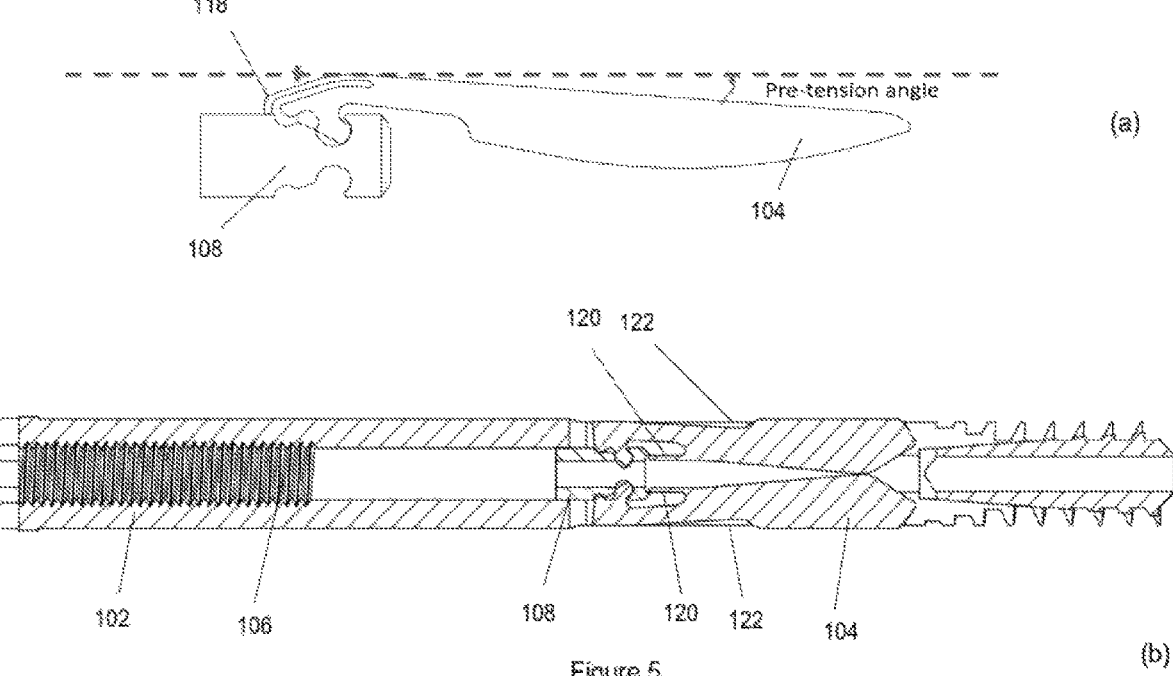

FIGS. 5(a) and 5(b) illustrate further components of the fastener 100 and again like components are given like reference numerals. FIG. 5(a) shows an expansion portion 104 with a cantilever spring element 118 and the coupling element 108. The spring element 118 biases the expansion portions 104 towards an unexpanded configuration to keep the expansion portions 104 within the dimension of the fastener 100, which is advantageous for insertion and removal of the fastener into a bore hole in bone (and/or through a portion of an orthopaedic nail or plate).

FIG. 5(b) shows an expansion portion 104 in accordance with a further variation. In this example the expansion portion 104 has inner cantilever-like spring element 120. The coupling member 108 has a recess 123 at an end portion into which ends of the spring element 120 engage whereby the expansion portions 104 are then also biased towards an unexpanded configuration.

The spring elements 118 and 120 are arranged to increase friction between the inner surface of the expansion portions 104 and the actuating element 110, which further facilitates moving the expansion portions 104 from the expanded configuration towards the normal or unexpanded configuration when the actuator 106 is moved along the axis of the body in a direction out of the body 102 to remove the fastener 100.

The expansion portions as shown in FIG. 5(b) further comprise outer recesses 122 which are positioned to reduce likelihood of jamming with a wall portion of an orthopaedic nail or plate when the expansion portions 104 are expanded or retracted and the fastener is moved out of the bore hole and through a portion of the orthopaedic nail, plate or another orthopaedic device.

Figure 6:
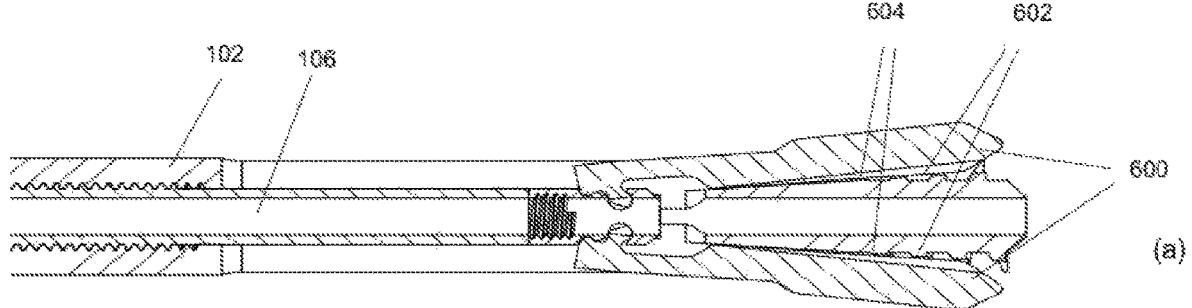
Figure 6:
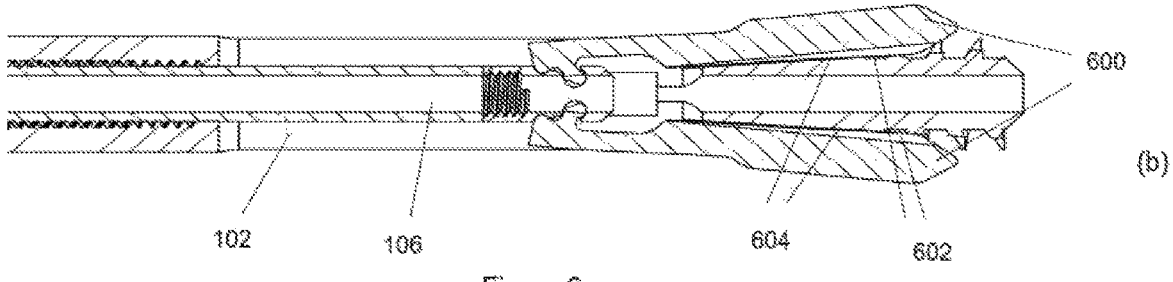
Figure 7:
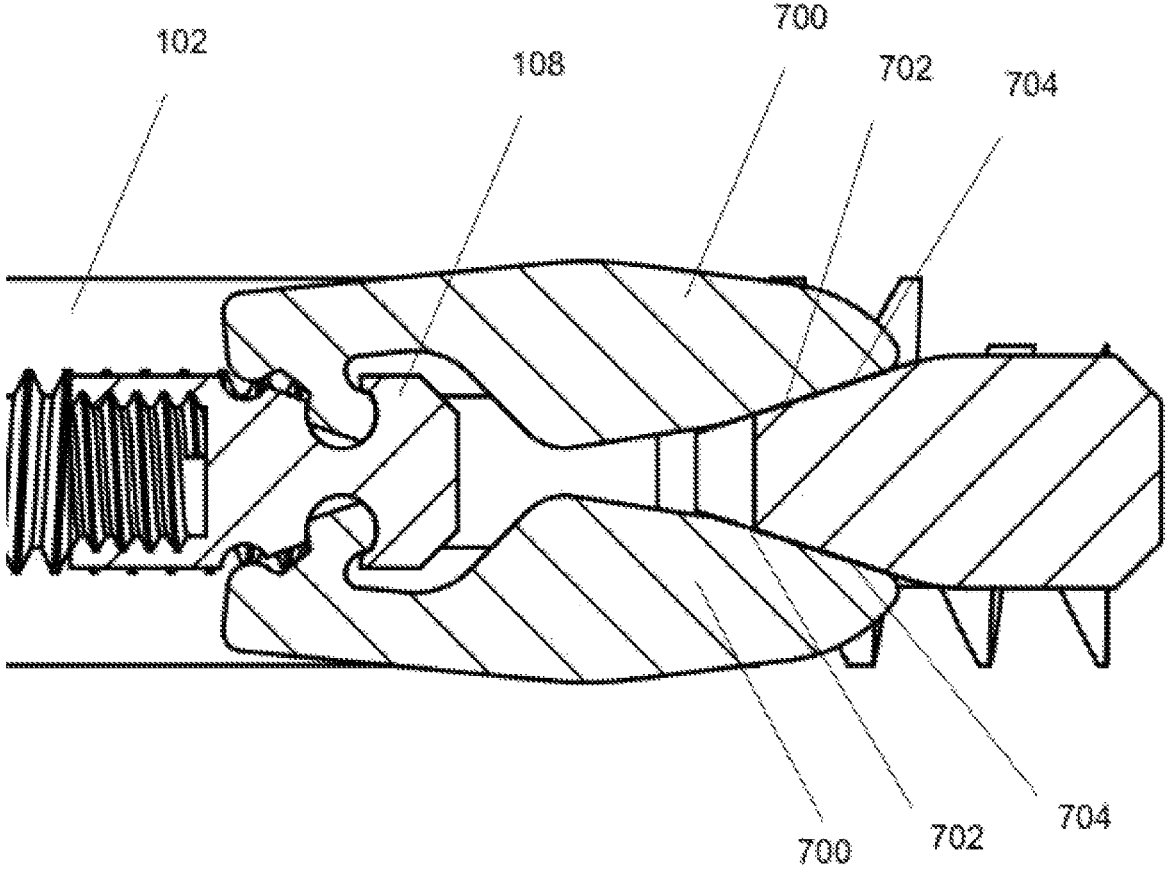

FIGS. 6 and 7 illustrate additional features of the fastener in accordance with embodiments of the present invention. Like components are given like reference numerals. FIG. 6(a) shows the fastener in the fully expanded configuration and FIG. 6(b) shows the fastener in a partially expanded configuration. In this embodiment the fastener comprises expansion portions 600 having inner expansion surfaces 602 and the actuating element 106 has actuating surface portions 604. The expansion surfaces 602 glide over the actuating surface portions 604 when the expansion portions 600 are moved towards the expanded configuration. The actuating surface portions 604 and the expansion surfaces 602 are shaped such that the actuating surface portions 604 and the expansion surfaces 602 are in contact over an extended area and have in this embodiment matching surface profiles, which avoids ingrowth of bone between the expansion surfaces 602 and actuating surface portions 604.

FIG. 7 shows components of a fastener according to a further embodiment of the present invention. The fastener comprises expansion portions 700, which have distal ends that are shaped such that no gap is formed between expansion surfaces 702 at the distal ends of the expansion portions 700 and the actuating surface portions 704 as long as the expansion surfaces 702 at distal ends of the expansion portions 700 glide entirely on the actuating surface portions 704 when the expansion portions 700 are moved into the expanded configuration, which results in bone being pushed by the distal ends of the expansion portions 700 along the actuating surface portions 704 rather than being caught between the expansion portions 700 and the actuating surface portions 704. The distal ends of the expansion portions 700 have a substantially flat or only slightly curved end surface portion 703 positioned and shaped such that bone is compacted at the distal ends of the expansion portion 700 when the expansion portion 700 is moved from the unexpanded configuration to the expanded configuration when the fastener is positioned in a bore hole in bone. The compacted bone provides reinforcement and may also stimulate bone growth to the area surrounding the distal ends of the expansion portion 700.

Further, the distal ends or tips of the expansion portions may have modified external surfaces arranged to promote growth of bone at the distal end or tip to prevent migration of the fastener and/or the orthopaedic device which the fastener in use fastens in bone further into bone than desired when pressure is applied (for example to prevent screw migration upwards into the hip joint when a patient walks after hip joint surgery). For example, the modified external surface of the expansion portion may have a coating comprising hydroxyapatite or may have an increased surface porosity to promote bone growth at the distal end or tip of the expansion portion. The location of the surface modification can be tailored to maximise fixation strength, for example on the upper side (cranial side) of the expansion portion to stop migration.

Figure 8:
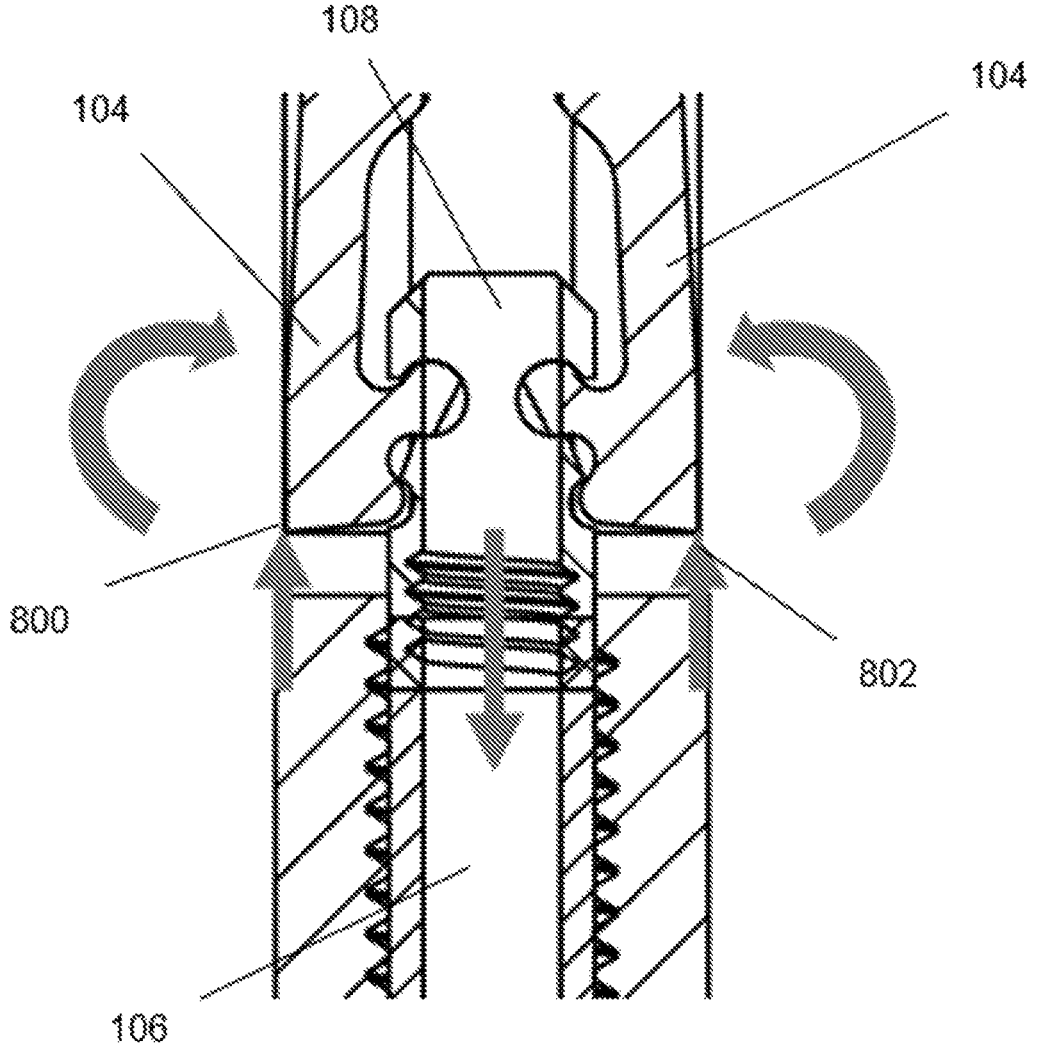

FIG. 8 shows a further variation of components of the fastener and again like components are given like reference numerals. The expansion portions 104 have in this embodiment edges 800, 802 formed by surfaces positioned at acute angles relative to each other. When the coupling member 108 is moved along the axis of the body in a direction away from the actuating element within the body 102 to retract the expansion portions 104, the edges 800, 802 in the slot of the body 102, abutting against the portion of the body 102, cause a rotation of the expansion portions 104 (which are coupled to the coupling member 108) towards an unexpanded configuration as indicated by arrows in FIG. 8, which facilitates ease of removal of the fastener.

The slots of the fasteners in all of the described embodiments and through which the expansion portions project when the expansion portions are in the expanded configuration (a slot may be seen in FIG. 1(a)) are shaped such that a gap between the expansion portions and wall portions of the slots of the body 102 is between 20-500 µm. The design of the above-described coupling member 108, the actuating surfaces and expansion surfaces, the cross-sectional shape of the expansion portions and the shape of the slots are all selected such that ingrowth of bone into the fastener is avoided.

A person skilled in the art will appreciate that various modifications of the described embodiment are possible. For example, in a variation of the described embodiments the coupling member may not comprise a separate recess for receiving a respective projection of an expansion portion, but may alternatively comprise a single ring-shaped recess or groove for receiving a plurality of the projections. In a further variation the coupling member may comprise the projections and the expansion portion may each comprise a corresponding recess. Reference that is being made to U.S. Ser. No. 10/729,480 does not constitute an admission that U.S. Ser. No. 10/729,480 is part of the common general knowledge of a skilled person in Australia or any other country.

The invention claimed is:

1. An expandable fastener for orthopaedic applications, the fastener being arranged for fastening when positioned in a bore hole in bone and comprising:

a body having an axis;

an expansion portion moveable between a contracted configuration and an expanded configuration and arranged such that the expansion portion is configured to urge outwardly from the axis of the body towards the bone surrounding the bore hole when moving towards the expanded configuration;

a coupling member for coupling to the expansion portion, the coupling member being moveable along the axis of the body; and an actuator movable along the axis of the body and arranged to move the coupling member along the axis of the body;

wherein one of the coupling member and the expansion portion comprises a recess and the other one of the coupling member and the expansion portion comprises a projection, and wherein the projection and the recess are arranged such that a hinge is formed when the projection is received in the recess and the expansion portion is movable about an axis through the projection, and wherein the projection is insertable into the recess in a first angular orientation of an axis of the expansion portion relative to the axis of the body and is prevented from retracting out of the recess in a second angular orientation of the axis of the expansion portion relative to the axis of the body, and a blocking portion configured to be moveable relative to the coupling member into a blocking configuration, wherein the blocking portion is positioned to block movement of the expansion portion into the first angular orientation when the expansion portion is in the expanded configuration thereby preventing that the expansion portion can de-couple from the coupling member, the blocking portion being arranged for blocking the expansion portion from over-expanding when in the blocking configuration.

2. The fastener of claim 1 comprising an actuating element positioned such that, when the coupling member and the expansion portion are moved towards the actuating element and the expansion portion contacts the actuating element, further movement of the expansion portion towards the actuating element urges an end of the expansion portion away from the axis of the body to transfer the expansion portion into the expanded configuration.

3. The fastener of claim 2 wherein the actuating element has an actuating surface and the expansion portion has an inner expansion surface that glides on the actuating surface when the expansion portion transitions from the contracted configuration, or from a configuration of minimal or no expansion, towards the expanded configuration, and wherein the actuating surface and the inner expansion surface have matching shapes at a contact area within which the inner expansion surface glides over the actuating surface whereby likelihood of penetration of the bone between the inner expansion surface and the actuating surface is configured to be reduced or the penetration of the bone is configured to be avoided when the expansion portion is moved towards the expanded configuration in the bone, and wherein the fastener is arranged such that the actuating surface and the inner expansion surface are always in contact when the expansion portion transitions to the expanded configuration.

4. The fastener of claim 2 wherein the blocking portion is shaped to frictionally engage with an inner surface of the expansion portion when the expansion portion is in the expanded configuration and, because of the frictional engagement, the expansion portion is moved from the expanded configuration towards the contracted configuration when the actuator is moved along the axis of the body in a direction out of the body and away from the actuating element.

5. The fastener of claim 1 wherein the body comprises a slot and the expansion portion projects through the slot when the expansion portion is in the expanded configuration and wherein the expansion portion and the slot are shaped such that the expansion portion contacts the slot or wherein the slot and the expansion portion form a gap of 20-500 μm thereby configured to reduce likelihood of, or to prevent, ingrowth of bone.

6. The fastener of claim 5 wherein the expansion portion is shaped such that the bone is configured to be pushed away by the expansion portion when moved towards the expanded configuration whereby the expansion portion and/or the slot are arranged such that bone accumulation at the expansion portion inside the slot is substantially avoided.

7. The fastener of claim 5 wherein the expansion portion has an outer surface that is curved in a plane perpendicular to the axis of the expansion portion and shaped to approximate a curvature of the body of the fastener in a plane perpendicular to the axis of the body whereby the expansion portion is arranged such that, when in the contracted configuration catching of the bone by the expansion portion or portions of the slot is substantially avoided when the fastener is removed from the bore hole in the bone.

8. The fastener of claim 1 wherein the expansion portion is one of a plurality of expansion portions.

9. The fastener of claim 1 wherein in the contracted configuration, the axis of the expansion portion is oriented along the axis of the body and wherein the fastener is configured such that movement of the expansion portion from the contracted configuration to an orientation across the axis of the body is necessary to reach the first angular orientation at which the expansion portion can be decoupled from the coupling member.

10. The fastener of claim 1 wherein the recess and/or the projection are shaped such that surfaces of the projection and the recess frictionally engage with each other when the projection is positioned within the recess and friction between the projection and the recess increases when the expansion portion is moved towards the expanded configuration from the contracted configuration.

11. The fastener of claim 1 wherein the blocking portion is provided in the form of an end portion of the actuator which is insertable into the body of the fastener and which is in the blocking configuration when inserted and positioned adjacent to the expansion portion.

12. The fastener of claim 1 wherein the fastener is arranged for projecting through a portion of an orthopaedic nail or another orthopaedic device and the expansion portion has an outer recess arranged to reduce likelihood of jamming with a wall portion of the orthopaedic nail or the another orthopaedic device when the expansion portion moves from the expanded configuration towards the contracted configuration to enable retraction of the fastener out of the bore hole and through the portion of the orthopaedic nail or the another orthopaedic device.

13. The fastener of claim 1 wherein the expansion portion comprises a lock-stop portion at which the expansion portion abuts with another portion of the fastener when the expansion portion is in the expanded configuration, wherein the lock-stop portion is arranged to avoid over expansion of the expansion portion and configured to minimize a gap between the expansion portion and the another portion of the fastener thereby reducing likelihood of ingrowth of bone.

14. The fastener of claim 1 comprising a spring-loaded mechanism which biases the expansion portion away from the expanded configuration towards the contracted configuration.

15. The fastener of claim 1 wherein the expansion portion has a distal portion or tip that is shaped such that the bone is configured to be compacted at the distal portion when the expansion portion is moved from the contracted configuration to the expanded configuration when the fastener is positioned in the bore hole in the bone.

16. The fastener of claim 1 wherein the expansion portion has a modified external surface at a distal end or tip of the expansion portion and the modified external surface is configured to promote growth of bone at the distal end or tip to prevent migration of the fastener, and/or an orthopaedic device which the fastener in use is configured to fasten in the bone, further into the bone than desired when pressure is applied.

17. The fastener of claim 1 wherein the expansion portion has a surface that abuts against another surface of the fastener and is shaped such that the expansion portion is moved from the expanded configuration towards the contracted configuration when the coupling member with the actuator is moved along the axis of the body and in a direction out of the body of the fastener.

* * * * *